United States Patent
Johansen et al.

(10) Patent No.: US 6,383,164 B1
(45) Date of Patent: May 7, 2002

(54) MASSAGING BREAST PUMP AND FUNNEL THEREFOR

(75) Inventors: Jean L. Johansen; Brenda J. Meyers, both of Reedsburg, WI (US); Alice A. Mensch; Patrick A. McCormick, both of Chicago, IL (US); Mark P. Slaven, Evanston, IL (US)

(73) Assignee: Gerber Products Company, Reedsburg, WI (US)

( * ) Notice: Subject to any disclaimer, the term of this patent is extended or adjusted under 35 U.S.C. 154(b) by 21 days.

(21) Appl. No.: 09/669,277

(22) Filed: Sep. 26, 2000

(51) Int. Cl.[7] .................................................. A61M 1/06
(52) U.S. Cl. ...................................................... 604/74
(58) Field of Search ........................ 604/73–76, 35–38, 604/132, 133, 346; D24/109

(56) References Cited

U.S. PATENT DOCUMENTS

| | | |
|---|---|---|
| 798,893 A | 9/1905 | Ezell |
| 2,542,505 A | 2/1951 | Gascoigne ................. 128/281 |
| 2,616,417 A | 11/1952 | Holbrook .................... 128/38 |
| 3,822,703 A | 7/1974 | Davisson ................... 128/281 |
| 4,583,970 A | 4/1986 | Kirchner ...................... 604/74 |
| 4,673,388 A | 6/1987 | Schlensog et al. ............ 604/74 |
| 4,680,028 A | 7/1987 | Stuart .......................... 604/74 |
| 4,705,504 A | 11/1987 | Viers ........................... 604/75 |
| 4,740,196 A | 4/1988 | Powell ......................... 604/75 |
| 4,759,747 A | 7/1988 | Aida et al. ................... 604/74 |
| 4,761,160 A | 8/1988 | Vermillion ................... 604/76 |
| 4,772,262 A | 9/1988 | Grant et al. .................. 604/74 |
| 4,794,915 A | 1/1989 | Larsson ....................... 128/64 |
| 4,799,922 A | 1/1989 | Beer et al. .................... 604/74 |
| 4,813,932 A | 3/1989 | Hobbs .......................... 604/74 |
| 4,857,051 A | 8/1989 | Larsson ....................... 604/74 |
| 4,883,464 A | 11/1989 | Morifuki ...................... 604/74 |
| 4,892,517 A | 1/1990 | Yuan et al. ................... 604/74 |
| 4,929,229 A | 5/1990 | Larsson ....................... 604/74 |
| 4,950,236 A | 8/1990 | Wilson ......................... 604/74 |
| 4,961,726 A | 10/1990 | Richter ........................ 604/74 |
| 4,964,851 A | 10/1990 | Larsson ....................... 604/74 |
| 5,007,899 A | 4/1991 | Larsson ....................... 604/74 |
| 5,009,638 A | 4/1991 | Riedweg et al. ............. 604/74 |
| 5,049,126 A | 9/1991 | Larsson ....................... 604/74 |
| 5,071,403 A | 12/1991 | Larsson ....................... 604/74 |
| 5,100,406 A | 3/1992 | Panchula ..................... 606/74 |
| 5,295,957 A | 3/1994 | Aida et al. ................... 604/74 |
| 5,304,129 A | 4/1994 | Forgach ....................... 604/74 |
| 5,358,476 A | 10/1994 | Wilson ......................... 604/74 |
| 5,415,632 A | 5/1995 | Samson ....................... 604/74 |
| 5,542,921 A | 8/1996 | Meyers et al. ............... 604/74 |
| 5,843,029 A | 12/1998 | Bachman et al. ............ 604/74 |
| 5,885,246 A | 3/1999 | Ford ............................ 604/74 |
| 5,941,847 A | 8/1999 | Huber et al. ................. 604/74 |
| 6,004,288 A | 12/1999 | Hochstedler et al. ........ 604/74 |
| D446,852 S * | 8/2001 | Johansen et al. .......... D24/109 |
| D446,853 S * | 8/2001 | Johansen et al. .......... D24/109 |
| 6,273,868 B1 * | 8/2001 | Nordvik ....................... 604/74 |

FOREIGN PATENT DOCUMENTS

| | | |
|---|---|---|
| BE | 524638 | 12/1953 |
| DE | 2807-646 | 8/1978 |
| DE | 3047-440 | 7/1982 |
| EP | 0 237 474 A | 9/1987 |
| EP | 0 466 462 A1 | 1/1992 |
| GB | 2 191 700 A | 12/1987 |

* cited by examiner

*Primary Examiner*—Sharon Kennedy
(74) *Attorney, Agent, or Firm*—Drinker Biddle & Reath LLP

(57) ABSTRACT

A breast pump funnel is disclosed. The funnel is shaped and dimensioned to fit a woman's breast, and has a neck to receive the nipple, a cup to fit over an inner part of the breast and a plurality of fingers extending outwardly from the cup to contact an outer part of the breast. The pump section of the breast pump is connected to the neck of the funnel to apply a varying suction to draw milk from the breast and to deliver the milk into a receiving vessel. The tips of the fingers of the funnel serve to massage the breast and stimulate the release of milk from the breast during pumping.

24 Claims, 5 Drawing Sheets

MASSAGING BREAST PUMP AND FUNNEL THEREFOR

FIELD OF THE INVENTION

The present invention is generally related to breast pumps for extracting milk from the breasts of human females. More particularly, the present invention is related to a funnel for such a pump that is designed to massage the breast in order to promote the flow of milk.

BACKGROUND OF THE INVENTION

For various reasons, a lactating woman may wish to extract and collect her milk, and pumps designed for that purpose are well known. Such a pump typically comprises a cup or funnel that fits over the breast and a neck into which the nipple fits. The other end of the neck is connected to an intake of the actual pumping mechanism, which may be electric or hand operated. If the pump is hand operated, it maybe a reciprocating pump having a trigger that is repeatedly squeezed to alternately suck milk from the breast and discharge it into a receiving bottle.

However, the human breast is adapted to respond optimally to suckling by a human baby, whose lips tend to move rhythmically as the baby suckles, massaging the breast. This massaging action stimulates the discharge of milk. Merely attempting to suck milk from the nipple is much less effective, because the breast does not respond well.

In the commercial milking of cattle, it has for many years been normal practice for the teat cups of a milking machine to have flexible liners. By cyclically changing the pressure in the space outside the liner, the milking machine massages the teats, encouraging the flow of milk. However, such machines, which typical rely on a separate pulsed air line for the massaging, are not usually very practical for use on human beings.

U.S. Pat. No. 5,885,246 describes a flexible insert for the funnel of a breast pump. The insert has a number of recesses in its outer surface, forming chambers between the insert and the funnel, which are in communication with the neck of the funnel, and are separated from the breast by thin bottom walls. Thus, as the suction delivered by the pump varies cyclically, the chambers expand and contract, and the bottom walls of the recesses move in and out, massaging the breast. However, the insert is a complex and expensive molding, and may be prone to fatigue because the thin bottom walls of the chambers are in continual movement. In addition the chambers, into which milk can penetrate, may present a hygiene problem if the insert is not removed and carefully cleaned after use, but if removed from the funnel the insert is very vulnerable to damage.

U.S. Pat. No. 5,100,406 describes a similar construction to the '246patent in which the chambers are vented to the exterior. This device apparently relies on the pump suction causing a cyclically varying vacuum in the space between the funnel insert and the breast.

SUMMARY OF THE INVENTION

The present invention is directed to a funnel for a breast pump, and a breast pump including such a funnel, that can effectively massage the breast.

The invention provides a funnel for a breast pump that fits over the nipple, and that has several fingers extending from the outer edge of the funnel and positioned to massage the breast and to stimulate the release of milk from the breast ducts.

The fingers need not all be of the same length. Preferably, they are of two different lengths alternately, to massage different parts of the breast. The fingers may be generally spoon-shaped, with the bowl of the "spoon" forming the tip of the finger, and the convex surface of the bowl contacting the breast. The tips of the fingers may be formed with small bumps to enhance the stimulating effect of the massage.

The inside of the funnel, including the fingers, maybe overmolded with a soft rubber material. Instead, a separate rubber insert may be provided, which should cover only the neck and the inner part of the funnel, and should stop short of the finger tips.

BRIEF DESCRIPTION OF THE DRAWINGS

For the purpose of illustrating the invention, the drawings show forms of the invention which are presently preferred. However, it should be understood that this invention is not limited to the precise arrangements and instrumentalities shown in the drawings.

DETAILED DESCRIPTION OF THE DRAWINGS

Figure 1:
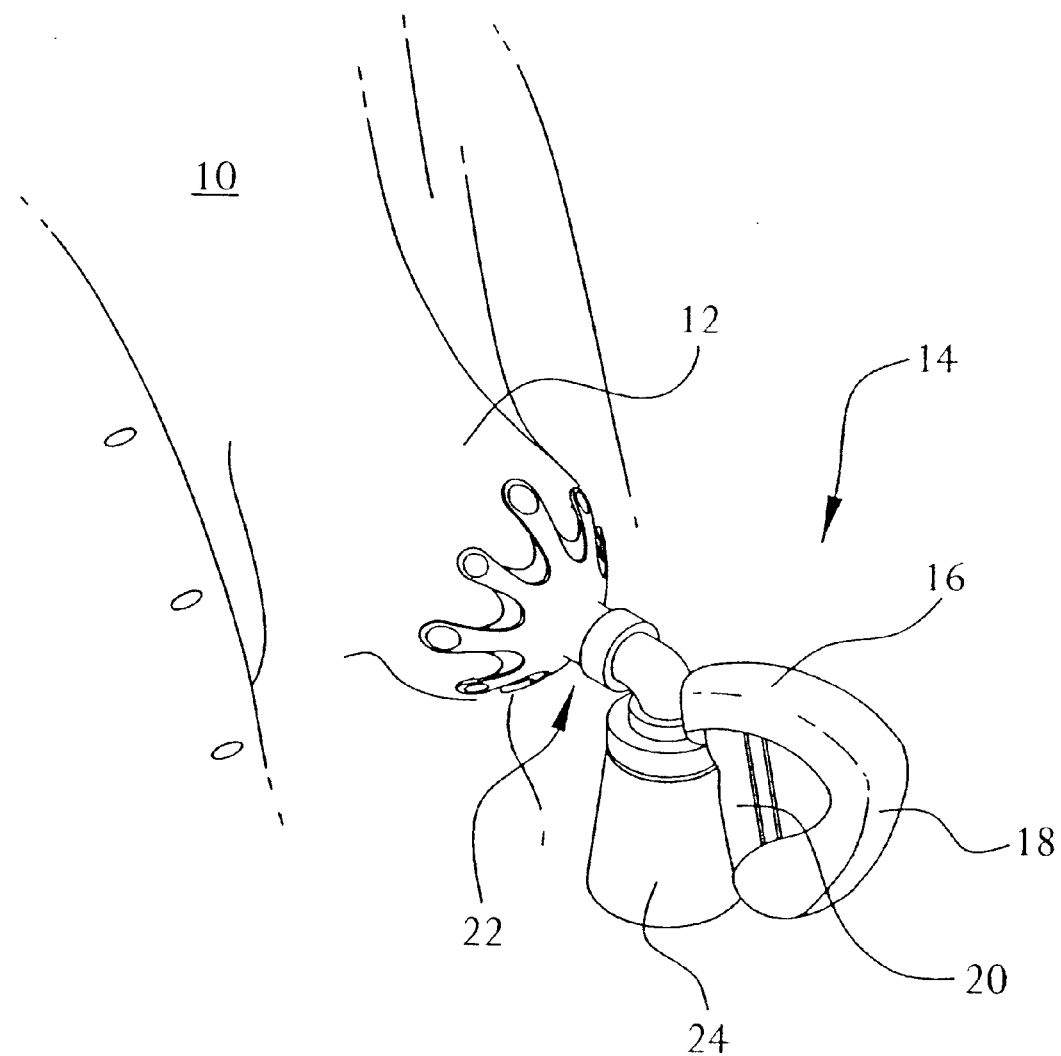
FIG. 1 is a perspective view of a pump with a funnel according to the present invention in place on a woman's breast.

Referring to the drawings, FIG. 1 illustrates a woman, indicated generally by the reference number 10, to whose breast 12 there is applied a breast pump, indicated generally by the reference number 14. The breast pump 14 comprises a pump section 16, a grip 18 and a trigger 20. The pump section is caused to operate by repeatedly squeezing together and releasing the trigger 20 and the grip 18. The pump section 16 serves to draw milk from a funnel indicated generally by the reference number 22 and to discharge the milk into a collecting bottle 24.

Figure 2:
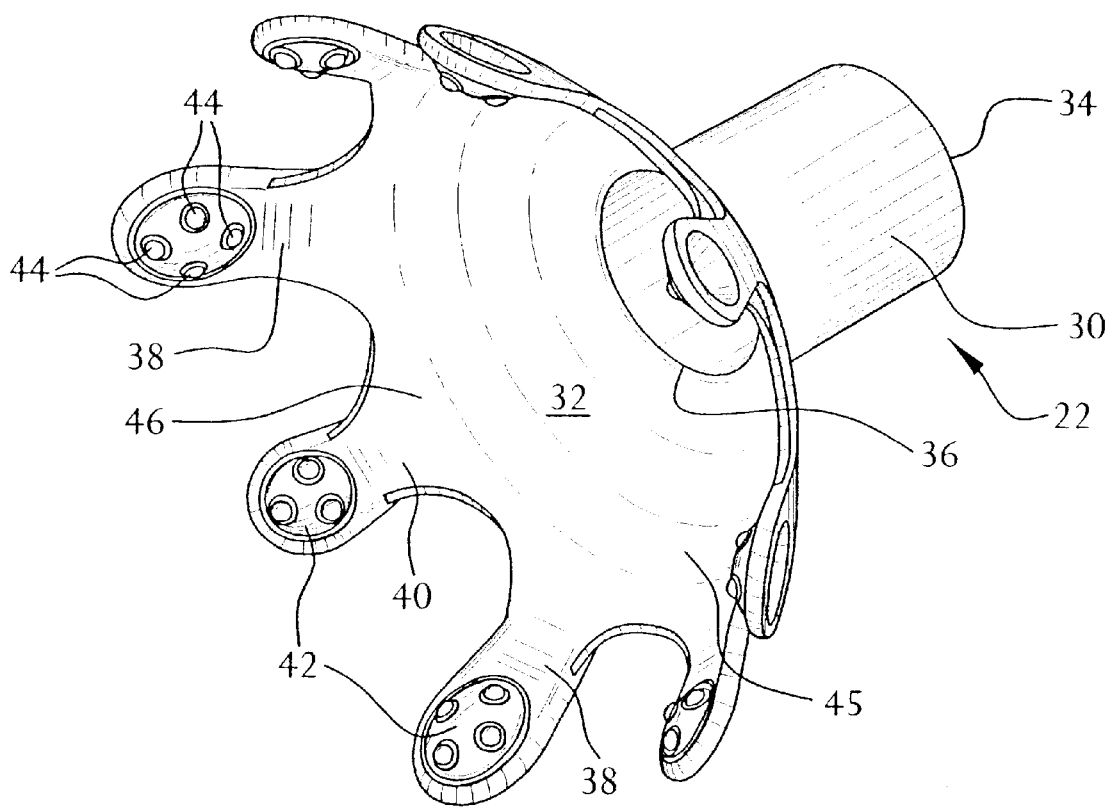
FIG. 2 is a perspective view of a first embodiment of a funnel according to the invention.
Figure 3:
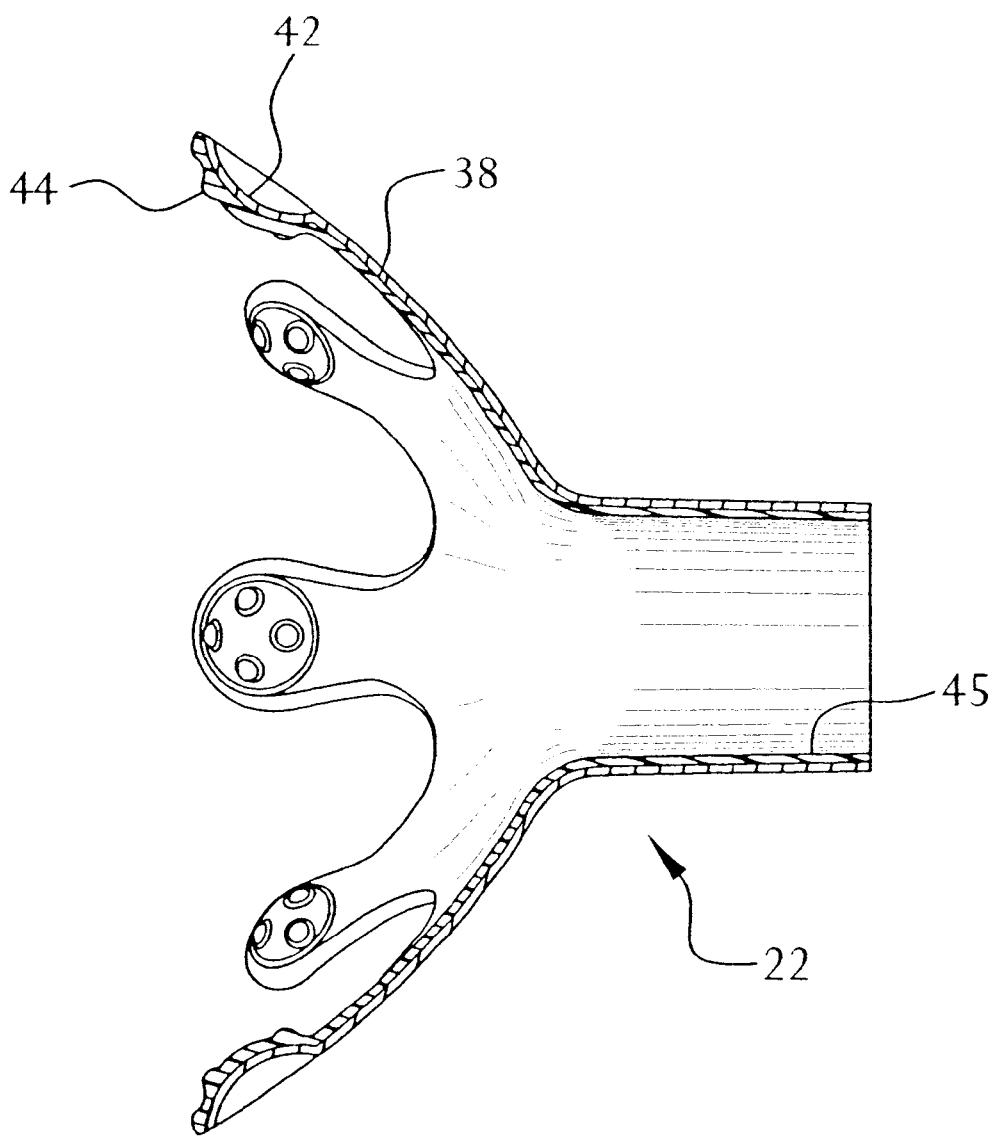
FIG. 3 is an axial cross-section through the funnel shown in FIG. 2.

Referring now also to FIGS. 2 and 3, the funnel 22 comprises a neck 30 and a cup 32. The end 34 of the neck 30 further from the cup 32 connects with the pump section 16. The other end 36 of the neck 30 is shaped and dimensioned to fit closely round the nipple (not shown) of the woman 10, and fairs smoothly into the cup 32, which is shaped and dimensioned to fit over the inner part of the woman's breast 12.

At the outer rim of the cup 32, there are projecting fingers 38, 40, which are shaped and dimensioned to extend outwards over the breast. The fingers 38, 40 are evenly spaced round the rim of the cup 32. There are an even number of fingers, and alternate fingers 38 are longer than the other four fingers 40. In this embodiment there are eight fingers, four longer fingers 38 and four shorter fingers 40. Each finger 38, 40 has at its tip a bowl 42, convex towards the inside of the funnel, that is positioned to press lightly on the breast 12 when the pump 10 is in position on the breast. Each bowl 42 may have on it a number of small bumps 44.

As may be seen from FIGS. 2 and 3, the fingers 38, 40 are continuations of the curve of the cup 32, and are comparatively broad and not particularly thick. They are not ribbed or otherwise stiffened. This affords a slight degree of flexibility, allowing the tips to spread apart resiliently. The tips of the fingers 38, 40 are rounded which, in combination with the curve of the bowls 42, allows the funnel to be placed onto the breast without the fingers digging into the flesh. The diameter of the funnel, measured across the tips of the longer fingers 38, may be 3.74" (95 mm).

The funnel 22 is made of rigid polypropylene or other suitable plastic material, and is overmolded on its inner side with a layer 45 of softer material. The softer material may be a thermoplastic elastomer synthetic rubber sold by Shell under the Trademark KRATON. Instead, it maybe the styrenic block copolymer sold by The Geon Company, of Avon Lake, Ohio, under the Trade Mark SYNPRENE IT38-074 TURQUOISE 6385, Product No. J3807 40A 9485, Recipe No. 001. The rubber is allowed to form webs 46 between the bases of the fingers 38,40. The rubber covers the entire inner sides of the fingers 38,40, including the tips with the bowls 42 and the bumps 44. However, the webs 46 do not extend more than a short way along the fingers 38, 40. The rubber 45 coats the inner side of the funnel 22 and is bonded to the plastic of the funnel 22 over its entire inner surface, preferably leaving no space therebetween.

Figure 4:
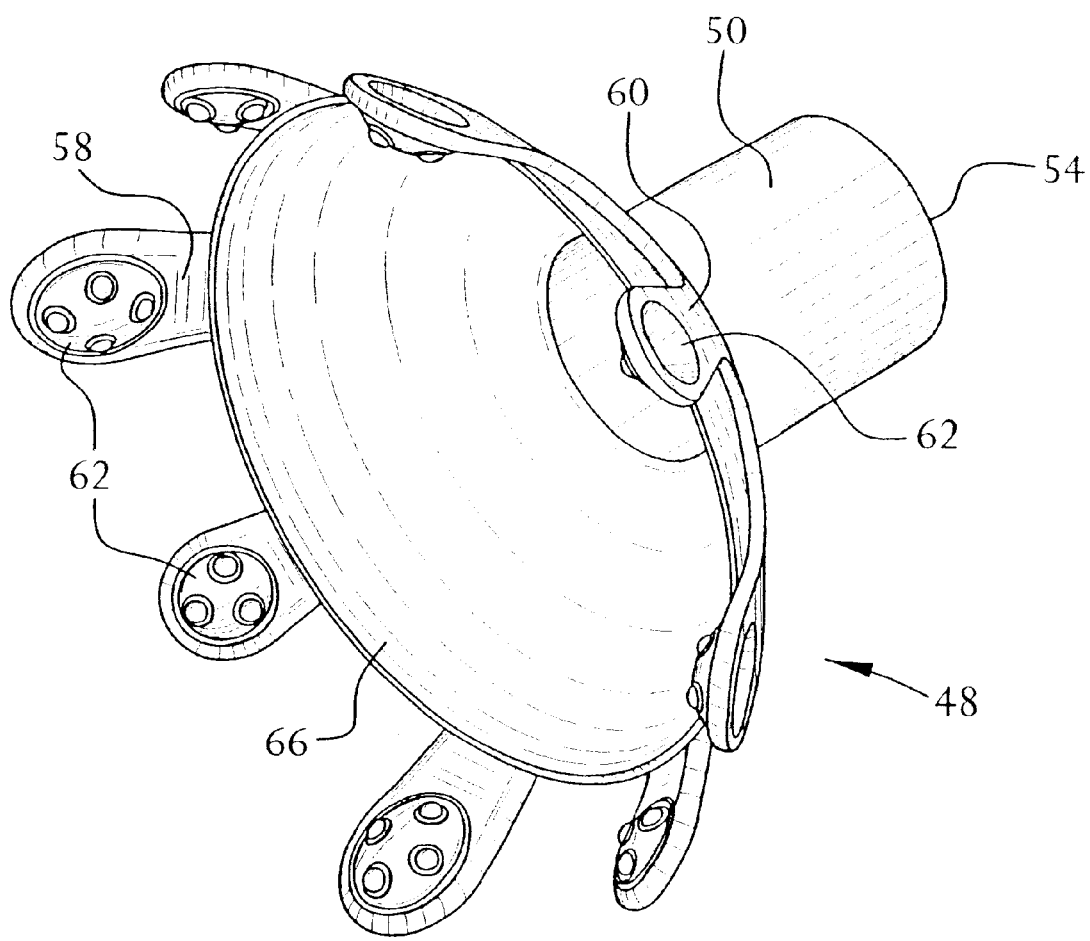
FIG. 4 is a perspective view of a second embodiment of a funnel according to the invention.
Figure 5:
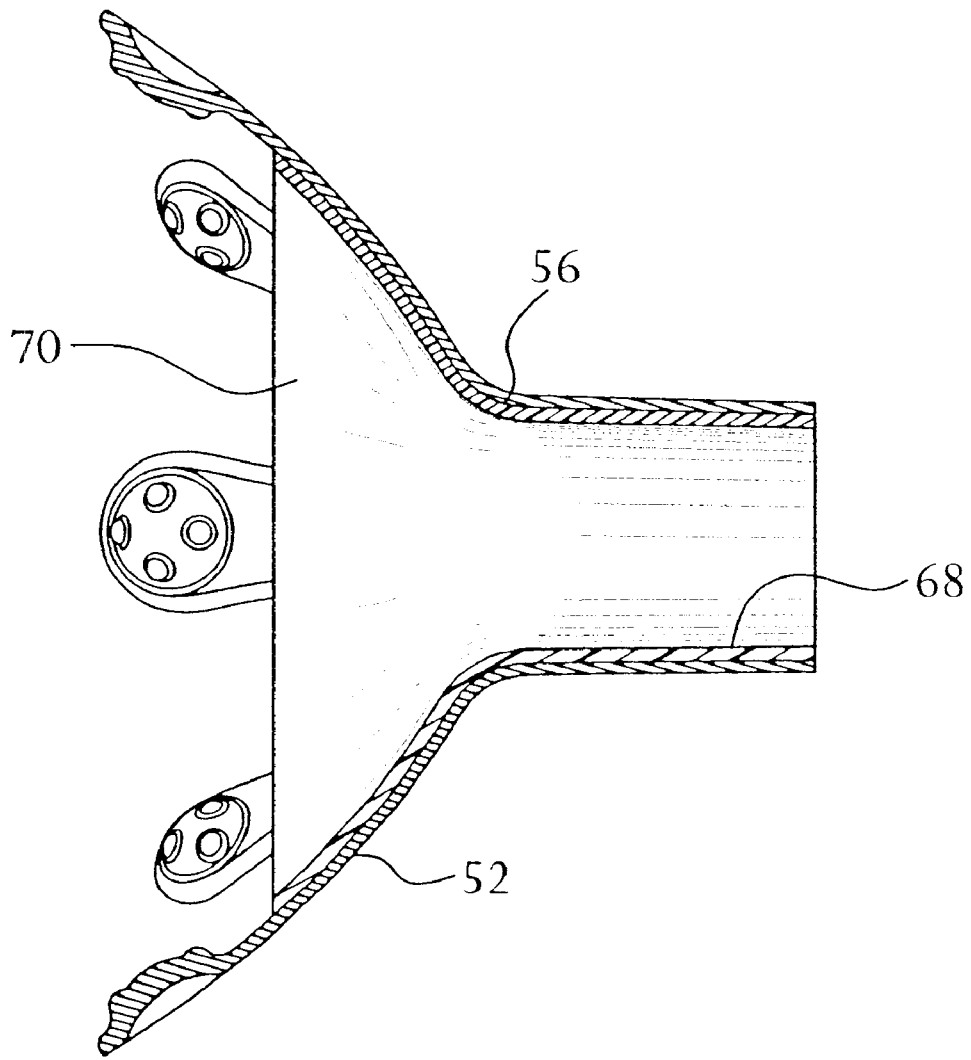
FIG. 5 is an axial cross-section through the funnel shown in FIG. 4.

Referring now to FIGS. 4 and 5, the second embodiment of funnel, indicated generally by the reference number 48, is similar to the first. The funnel 48 has a neck 50 and a cup 52. The end 54 of the neck 50 further from the cup 52 connects with the pump section 16. The other end 56 of the neck 50 is dimensioned to fit closely round the nipple (not shown) of the woman 10, and fairs smoothly into the cup 52, which is arranged to fit over the woman's breast 12.

At the outer rim of the cup 52, there are a ring of evenly-spaced fingers 58, 60, which in this embodiment are eight in number. Four fingers 58 are longer than, and alternate with, the other four fingers 60. Each finger 58, 60 has at its tip a bowl 62, convex towards the inside of the funnel, that is positioned to press lightly on the breast 12 when the pump 10 is in position on the breast. Each bowl 62 has on it a number of small bumps 64.

The funnel 48 is made of relatively rigid material, such as polypropylene. An insert 66 of softer material such as silicone rubber is fitted inside the funnel 48. The insert 66 is funnel shaped, and has a neck 68 that fits snugly within the neck of the funnel 48, and a cup 70 that fits within the cup 52 of the funnel 48. As shown in FIGS. 4 and 5, the cup 70 of the insert 66 may overlap the bases of the fingers 58, 60, but leaves the fingertips, including the bowls 62, uncovered so as not to interfere with the contact between the bowls and the breast. The insert lies against the inner surface of the funnel 48, with no space or air gap between them. The thickness of the insert 66 is preferably tapered at the rim of the cup 70, to reduce the height of the step formed where the rim overlies the fingers 58, 60, and the actual rim may be rounded. A radius of 0.755" (1.9 mm) has been found satisfactory. Apart from the tapered rim, the insert 66 may be essentially a conventional flexible funnel for use with a conventional breast pump. The intake of the pump unit of a conventional breast pump is typically a short tube, in which the neck of the funnel is a snug fit. In this embodiment, the tube may fit outside the neck 50 of the funnel 48, or between the neck 50 of the funnel 48 and the neck 70 of the insert 66.

In use, the woman 10 places the funnel 22 or 48 over her breast 12, with her nipple in the neck 30 or 50 of the funnel and with the cup 32 or 52 resting against her breast. The bowls 42 or 62 and the bumps 44 or 64 of the fingers press gently against the breast.

The woman then starts pumping by squeezing and releasing the trigger 20 and the grip 18, producing a reciprocating operation of the pump unit 16. The pump unit 16 alternately applies and releases suction to the funnel. This naturally causes a rhythmic movement of the pump 14 as a whole, including the tips of the fingers 38, 40 or 58, 60, causing the bowls 42 or 62, and the bumps 44 or 64 if present, to massage the breast. That massaging action simulates the massaging of the breast by a baby's mouth, and stimulates the release by the breast of milk, which is gathered up by the pump unit 16 and transferred to the collecting bottle 24.

Although the invention has been described and illustrated with reference to exemplary embodiments thereof, it will be understood by those skilled in the art that various changes, omissions, and additions may be made thereto without departing from the spirit and scope of the invention as recited in the attached claims.

What is claimed is:

1. A funnel for a breast pump, comprising:
    a neck portion shaped and dimensioned to receive the nipple of a woman's breast, and adapted to be connected to a pump section of the breast pump;
    a cup portion, shaped and dimensioned to fit over an inner part of the breast; and
    a plurality of fingers extending outwardly from the cup portion, and shaped and dimensioned to contact an outer part of the breast.

2. A funnel according to claim 1, wherein the tips of the fingers project inwardly to engage the breast.

3. A funnel according to claim 2, wherein the tips of the fingers are formed with bowls that are convex towards the breast.

4. A funnel according to claim 2, wherein the tip of each finger is formed with a plurality of bumps on a side towards the breast.

5. A funnel according to claim 1, wherein the fingers are of different lengths.

6. A funnel according to claim 5, wherein there are an even number of fingers, alternately of two different lengths.

7. A funnel according to claim 1, which is made of a rigid material coated on the inside with a relatively soft flexible material.

8. A funnel according to claim 7, wherein the softer material coats the inner surfaces of the tips of the fingers.

9. A funnel according to claim 1, which is made of a rigid plastic material and comprises an insert of a softer material on the inside.

10. A funnel according to claim 9, wherein the insert covers the inside of the cup of the funnel, and leaves the tips of the fingers uncovered.

11. A funnel according to claim 1, wherein the cup and neck portions are a single unitary piece, and the plurality of fingers include a separate cup portion.

12. A breast pump, comprising:
    a funnel shaped and dimensioned to fit a woman's breast, and having
        a neck shaped and dimensioned to receive the nipple of the breast,
        a cup shaped and dimensioned to fit over an inner part of the breast, and
        a plurality of fingers extending outwardly from the cup and shaped and dimensioned to contact an outer part of the breast, p1 a receiving vessel for breast milk; and
    a pump section connected to the neck of the funnel opposite the cup and to the receiving vessel and arranged to apply a varying suction to the funnel to draw milk from the breast and to deliver the milk into the receiving vessel.

13. A breast pump according to claim 12, wherein the pump section in operation alternately applies and releases suction.

14. A breast pump according to claim 12, wherein the pump is arranged to be operated manually by a reciprocating manipulation.

15. A breast pump according to claim 12, wherein the tips of the fingers project inwardly to engage the breast.

16. A breast pump according to claim 15, wherein the tips of the fingers are formed with bowls that are convex towards the breast.

17. A breast pump according to claim 15, wherein the tip of each finger is formed with a plurality of bumps on a side towards the breast.

18. A breast pump according to claim 12, wherein the fingers are of different lengths.

19. A breast pump according to claim 18, wherein there are an even number of fingers, alternately of two different lengths.

20. A breast pump according to claim 12, which is made of a rigid plastic material coated on the inside with a softer material.

21. A breast pump according to claim 20, wherein the softer material coats the inner surfaces of the tips of the fingers.

22. A breast pump according to claim 12, which is made of a rigid plastic material and comprises an insert of a softer material on the inside.

23. A breast pump according to claim 22, wherein the insert covers the inside of the cup of the funnel and the bases of the fingers, but leaves the tips of the fingers uncovered.

24. A breast pump according to claim 12, wherein the cup and neck portions are a single unitary piece, and the plurality of fingers include a separate cup portion.

* * * * *